United States Patent [19]

Marchosky et al.

[11] Patent Number: 4,989,601

[45] Date of Patent: Feb. 5, 1991

[54] METHOD, APPARATUS, AND SUBSTANCE FOR TREATING TISSUE HAVING NEOPLASTIC CELLS

[75] Inventors: Jose A. Marchosky, Creve Couer; Christopher J. Moran, St. Louis, both of Mo.; Neal E. Fearnot, West Lafayette, Ind.

[73] Assignee: Medical Engineering & Development Institute, Inc., West Lafayette, Ind.

[21] Appl. No.: 247,769

[22] Filed: Sep. 22, 1988

Related U.S. Application Data

[63] Continuation-in-part of Ser. No. 193,167, May 2, 1988, which is a continuation of Ser. No. 112,628, Oct. 22, 1987, abandoned, which is a continuation-in-part of Ser. No. 697,697, Feb. 4, 1985, Pat. No. 4,719,919, which is a continuation of Ser. No. 459,708, Jan. 21, 1983, abandoned.

[51] Int. Cl.$^5$ .................. A61F 7/00; A61M 37/00
[52] U.S. Cl. .................. 128/399; 128/401; 128/784; 604/51; 604/890.1; 604/892.1; 606/27; 606/31
[58] Field of Search .............. 128/399, 401, 783, 784, 128/804; 606/27, 28, 29, 30, 31; 604/265, 890.1, 891.1, 892.1, 51

[56] References Cited

U.S. PATENT DOCUMENTS

| | | | |
|---|---|---|---|
| 1,707,762 | 4/1929 | Homan . | |
| 2,777,445 | 1/1957 | Hart | 128/303.12 |
| 3,170,465 | 2/1965 | Henney et al. | 128/303.1 |
| 3,369,549 | 3/1968 | Armao | 128/303.1 |
| 3,901,224 | 8/1975 | Bucalo | 128/82.1 |
| 3,938,526 | 2/1976 | Anderson et al. | 128/303.1 |
| 3,942,535 | 3/1976 | Schulman | 128/419 PS |
| 3,949,388 | 4/1976 | Fuller | 128/903 |
| 4,030,499 | 6/1977 | Bucalo | 128/260 |
| 4,046,139 | 9/1977 | Horn | 128/736 |
| 4,106,488 | 8/1978 | Gordon | 128/399 |
| 4,142,529 | 3/1979 | Latenser et al. | 128/303.12 |
| 4,146,029 | 3/1979 | Ellinwood | 128/419 P |
| 4,223,678 | 9/1980 | Langer et al. | 128/903 |
| 4,227,535 | 10/1980 | Connor | 128/401 |

(List continued on next page)

Primary Examiner—Edward M. Coven
Assistant Examiner—Jessica J. Harrison
Attorney, Agent, or Firm—Richard J. Godlewski

[57] ABSTRACT

Method, apparatus, and a substance is disclosed for releasing at a temperature above normal tissue temperature an anti-cancer drug and applying heat in combination to tissue having neoplastic cells such as a malignant brain tumor. The apparatus comprises a probe having a semi-rigid elongated member that is interstitially implanted in the malignant tumor. The elongated member is coated with a carrier substance that is responsive at a temperature above normal tissue temperature for releasing a carried substance such as a therapeutic anti-cancer drug. Within the elongated member, an electrical heater element produces heat when energized for heating the probe, the carrier substance, the anti-cancer drug, and the surrounding tissue. An electrical thermistor is also included within the elongated member for measuring the temperature of the probe in order to regulate the release of the drug and the temperature of the surrounding tissue. The method includes interstitially implanting the elongated member of the probe in the tumor, energizing the electrical heater element, releasing the drug in response to the heat to effect one treatment, and heating the tissue and drug to effect a second treatment. The combination of the heat and drug treatments then has an effectiveness level greater than the effectiveness levels of the heat and drug treatments individually. The coating layer substance includes a combination of a carrier and a carried substance for releasing the carried substance at a predetermined temperature above normal tissue temperature.

39 Claims, 5 Drawing Sheets

FOREIGN PATENT DOCUMENTS

| | | | |
|---|---|---|---|
| 0048402 | 3/1982 | European Pat. Off. | 128/303.1 |
| 8402839 | 8/1984 | PCT Int'l Appl. . | |
| 998794 | 7/1965 | United Kingdom | 604/890.1 |
| 1143149 | 2/1969 | United Kingdom | 128/401 |
| 2130094 | 5/1984 | United Kingdom . | |
| 2153675 | 8/1985 | United Kingdom | 604/890.1 |

U.S. PATENT DOCUMENTS

| | | | |
|---|---|---|---|
| 4,232,679 | 11/1980 | Schulman | 128/419 PG |
| 4,239,040 | 12/1980 | Hosoya et al. | 128/213 R |
| 4,275,738 | 6/1981 | McDonald et al. | 128/419 PG |
| 4,312,364 | 1/1982 | Convert | 128/804 |
| 4,331,161 | 5/1982 | Patel | 128/399 |
| 4,333,469 | 6/1982 | Jeffcoat et al. | 128/784 |
| 4,360,028 | 11/1982 | Barbier et al. | |
| 4,465,069 | 8/1984 | Barbier et al. | |
| 4,483,341 | 11/1984 | Witteles | 128/303.1 |
| 4,558,690 | 12/1985 | Joyce | 128/804 |
| 4,572,214 | 2/1986 | Nordenstrom et al. | 128/785 |
| 4,577,642 | 3/1986 | Stokes | 128/784 |
| 4,591,496 | 5/1986 | Cohen et al. | 424/15 |
| 4,638,045 | 1/1987 | Kohn et al. | 530/323 |
| 4,642,111 | 2/1987 | Sakamoto et al. | 604/890.1 |
| 4,654,024 | 8/1987 | Crittenden et al. | 604/49 |
| 4,679,561 | 8/1987 | Doss | |
| 4,709,698 | 12/1987 | Johnson et al. | 128/303.12 |
| 4,719,919 | 1/1988 | Marchosky et al. | |
| 4,739,771 | 4/1988 | Manwaring | |
| 4,744,370 | 5/1988 | Harris | |
| 4,744,933 | 5/1988 | Rha et al. | 264/4.3 |
| 4,749,620 | 6/1988 | Rha et al. | 428/402.2 |
| 4,763,671 | 8/1988 | Goffinet | 128/804 |
| 4,781,676 | 11/1988 | Schweighardt et al. | 128/804 |
| 4,800,899 | 1/1989 | Elliott | 128/401 |
| 4,801,459 | 1/1989 | Liburdy | 128/804 |

OTHER PUBLICATIONS

"Combined Treatment of Solid Tumor by Local Hyperthermia and Actinomycin D", A. Yerushalmi, Br. J. Cancer (1978) 37,827.

Blackshear, "Implantable Drug Delivery Systems" Scientific American, Dec. 1979, pp. 66–73.

Hornback, Ned B., "Hyperthermia and Cancer", 1984, Chapter I, vol. I.

Storm, Kristian, "Hyperthermia in Cancer Therapy", 1983, Table of Contents.

Nussbaum, Gilbert H., "Physical Aspects of Hyperthermia", 1982, Table of Contents.

Parsonnet et al., "An Experimental Method for Thermal Control of Heart Rate: Work in Progress", Pace, Sep.–Oct., 1980.

Murawski et al., "An Externally Programmable, Implantable, Integrated Cerebellar Stimulator", IEEE in Medicine & Biology Society, 1982.

Taylor, "Brain Cancer Therapy Using an Implanted Microwave Radiator", Microwave Journal, 1981.

Sutton, Carl H., "Tumor Hyperthermia in the Treatment of Malignant Gliomas of the Brain", *Transactions of the American Neurological Association*, 96:195–199, 1971.

Anghileri, Leopold et al., [Eds.], *Hyperthermia in Cancer Treatment*, CRC Press, Inc., Boca Raton, Fla., 1986, pp. 26, 44, 126, 136–138.

Pacela et al., "New Copolymer Will Administer Brain Cancer Drug", *Biomedical Technology*, vol. 14, No. 24, Nov. 15, 1987, p. 244.

Mulcahy, "Hyperthermia and Chemotherapy", *Syllabus: A Categorical Course in Radiator Therapy: Hyperthermia*, Radiological Society of North America, No. 29–Dec. 4, 1987, pp. 27–35.

Tamargo et al., "Growth Inhibition of the 9L Gliosarcoma by the Local Sustained Release of BCNU: A Comparison of Systemic Versus Regional Chemotherapy", *Scientific Program the Meeting of the American Association of Neuroiogical Surgeons*, Apr. 24–28, 1988, Toronto, Ontario, p. 212.

Brem et al., "A Biodegradable Polymer for Intracranial Drug Delivery: A Radiological Study in Primates", *Scientific Program: The Annual Meeting of the American Association of Neurological Surgeons*, Apr. 24–28, 1988, Toronto, Ontario, pp. 381–382.

Brem et al., "Biocompatibility of a BCNU-Loaded Biodegradable Polymer: A toxicity Study in Primates", *Scientific Program: The Anual Meeting of the American Association of Neurological Surgeons*, Apr. 24–28, 1988, Toronto, Ontario, pp. 381–382.

Tamargo et al., "Brain Biocompatibility of a Biodegradable Polymer Capable of Sustained Release of Macromolecules", *Scientific Program: The Annual Meeting of the American Association of Neurological Surgeons*, Apr, 24–28, 1988, Toronto, Ontario, pp. 399–400.

Yang et al., "Sustained Systemic Delivery of BCNU from an Intraperitoneal Polymer Implant", *Scientific Program: The Annual Meeting of the American Association of Neurological Surgeons*, Apr. 24–28, Toronto, Ontario, p. 414.

Leong et al., "Bioerodible Polyanhydrides as Drug-Carrier Matrices. II. Biocompatibility and Chemical Reactivity", *Journal of Biomedical Materials Research*, vol. 20, 1986, pp. 51–64.

Leong et al., "Bioerodible Polyanhydrides for Cancer Chemotherapy", *Proceed. Intern. Symp. Control. Bioact. Mater.*, 12, 1985, pp. 106–107.

Rosen et al., "Bioerodible Polyanhydrides for Controlled Drug Delivery", *Biomaterials*, 1983, vol. 4, Apr., pp. 131–133.

Leong et al., "Bioerodible Polyandrides as Drug-Carrer Matrices. I: Characterization, Degradation, and Release Characteristics", *Journal of Biomedical Materials Research*, vol. 19, 1985, pp. 941–955.

Beck et al., "An Overview of the FDA Approved Controlled-Release Polymeric Materials", Proceed Intern. Symp. Control. Rel. Bioact. Mater., 12, 1985, p. 214.

Langer, Robert S., "New Drug Delivery Systems: What the Clinician Can Expect", *Drug Therapy*, Apr., 1983, pp. 217–231.

Langer, et al., "Biocompatibility of Polymeric Delivery Systems for Macromolecules", *Journal of Biomedical Materials Research*, vol. 15, 1981, pp. 267–277.

Kenealy, Dr. J., "Safety and Efficacy of BCNU Delivered from a Biodegradable", Surgically Implanted Polymer for the Treatment of Grade III or IV Astrocytoma, Protocol NPC8701, Nova Pharmaceutical Corp., pp. 1–15.

"Treatment of Grade III and IV Anaplastic Glioma by Means of Controlled Release of Carmustine (BCNU) from Biodel ®, a Biodegradable Polymer", Investigator's Brochure, Nova Pharmaceutical Corporation, Jul. 20, 1988, pp. 1–32.

Brem et al., "Biocompatibility of a Biodegradable, Controlled-Release Polymer in the Rabbit Brain", The John Hopkins University School of Medicine, Baltimore, MD, 1988.

Grossman et al., "The Intracerebral Delivery of BCNU with Surgically Implanted Biodegradable Polymers: A Quantitative Autoradiographic Study", Proceedings of ASCO, vol. 7, Mar. 1988, p. 84.

Weiss, Rick, "Delivering the Goods: Designing a New Drug is One Thing; Getting it to the Disease is Another", *Science News*, vol. 133, pp. 360–362, Jun. 1988.

Langer et al., "Controlled Release: Three Mechanisms", *Chemtech*, Feb., 1986, pp. 108–110.

Tamargo et al., "Brain Biocompatibility of a Biodegradable Controlled-Release Polymer in Rats", *Journal of Biomedical Materials Research*, vol. 00, 1988, pp. 00–00.

Leong et al., "Polyanhydrides for Controlled Release of Bioactive Agents", *Biometerial*, vol. 7, Sep. 1986, pp. 364–371.

Anghileri, Leopold et al., [Eds.], *Hyperthermia in Cancer Treatment*, (CRC Press, Boca Raton, Fla., 1986) vol. II:190–193, vol. III:25–45.

Hornback, Ned B., *Hyperthermia and Cancer*, (CRC Press, Boca Raton, Fla., 1984), vol. II, pp. 4–5, 18–21, and 96–97.

Nussbaum, Gilbert H. [Ed.], *Physical Aspects of Hyperthermia* (American Institute of Physics, New York, 1982), pp. 287–293, 300–305, 340–342, 368–370, and 495–534.

Storm, F. Kristian [Ed.], *Hyperthermia in Cancer Therapy*, (G. K. Hall Medical Publishers, Boston, 1983), pp. 270–274.

Moran, Christopher J. et al., "A Simple Stabilization Device for Intracranial Aspiraton Procedures Guided by Computed Tomography", *Radiology*, 144(1):183–184, Jul. 1982.

Moran, Christopher J. et al., "CT-Guided Needle Placement in the Central Nervous System: Results in 146 Consecutive Patients", *American Journal of Neuroradiology*, 5:419–426, Jul./Aug. 1984.

Marchosky, J. Alexander et al., "A Simple Stereotaxic CT-Controlled Brain System for General Neurosurgical Use", *Contemporary Neurosurgery*, 5(18):1–8, 1983.

Abrath, Fred G. et al., "Dosimetry of CT-Guided Volumetric IR-192 Brain Implant", *International Journal of Radiation Oncology, Biology Physics*, 12(3):359–363, Mar. 1986.

Taylor, Leonard S., "Implantable Radiators for Cancer Therapy by Microwave Hyperthermia", *Proceedings of the IEEE*, 68(1):142–149, Jan. 1980.

Taylor, Leonard S. "Electromagnetic Syringe", *IEEE Transaction of Biomedical Engineering*, BME-25(3):3-03–304, May 1978.

Seegenschmiedt, M. H. et al., "Optimized Clinical Pre--Treatment Planning of Intersitial Hyperthermia", North American Hyperthermia Group, Philadelphia, Apr. 16–21, 1988 (Abstract and handout).

Strohbehn, John W. et al., "Blood Flow Effects on the Temperature Distributions from an Invasive Microwave Antenna Array Used in Cancer Therapy", *IEEE Transaction on Biomedical Engineering*, BME-29(9):6-49–661, Sep. 1982.

Strohbehn, John W. et al., "Interstitial Microwave Antenna Array Systems for Hyperthermia", *Frontiers of Radiation Therapy & Oncology*, 18:70–74, 1984.

Lyons, Bernard E. et al., "Localized Hyperthermia in the Treatment of Malignant Brain Tumors Using an Interstitial Microwave Antenna Array", *IEEE Transactions on Biomedical Engineering*, BME-31(1):53–62, Jan. 1984.

Percy, J. F., "Heat in the Treatment of Carcinoma of the Uterus", Symposium on Cancer of the Uterus, Clinical Congress of Surgeons of North America, Boston, Oct. 25–30, 1915.

"Scientists Planting 'Seeds' in Tumors of Cancer Patients", *The Indianapolis Star*, Dec. 2, 1984.

McKinley, Edward, "Radioactive 'Seeds' Helping Methodist Fight Brain Tumors", *The Indianapolis Star*, p. 18, Mar. 28, 1985.

Robinson, Donald, "Are We Winning Against Cancer?", *Parade*, p. 17, Jun. 14, 1987.

"Heat: A Treatment Option for Some Cancers?", *New York Times Service*, 1988.

"Polymer Developed at MIT Incorporates Polyanhydrides for Biodegradable Implants", *Biomedical Technology*, 15(11):123, Jun. 1, 1988.

Yatvin et al., "Temperature-and pH-Sensitive Liposomes for Drug Targeting", *Methods in Enzymology*, vol. 149, pp. 77–87, 1987.

Heller J., "Use of Polymers in Controlled Drug Release", *Biocompatible Polymers, Metals, and Composites*, Technomic Publishing Co., Inc., Lancaster, Pa., 1983, Ch. 24, pp. 551–584.

Hornback, Ned B., "Hyperthermia and Cancer", (CRC Press, Inc., Boca Raton, Fla., 1984), vol. I, pp. 65–75, 95–107; vol. II, pp. 107–111, 131–133.

Song et al., "Heat and Blood Flow", *Annals New York Academy of Sciences*, pp. 45–47.

Storm, F. Kristian [Ed.], *Hyperthermia in Cancer Therapy*, (G. K. Hall Medical Publishers, Boston, 1983), Chapters 1, 2, 11 and 12.

Nussbaum, Gilbert H., [Ed.], *Physical Aspects of Hyperthermia*, (American Institute of Physics, New York, 1982), pp. 90–104, 280–356, 368–392, and 495–538.

METHOD, APPARATUS, AND SUBSTANCE FOR TREATING TISSUE HAVING NEOPLASTIC CELLS

CROSS-REFERENCE TO RELATED APPLICATIONS

This application is a continuation-in-part of application Ser. No. 193,167, filed May 2, 1988, which is a continuation of application Ser. No. 112,628, filed Oct. 22, 1987, abandoned, which is a continuation-in-part of application Ser. No. 697,697, filed Feb. 4, 1985, U.S. Pat. No. 4,719,919, which is a continuation of application Ser. No. 459,708, filed Jan. 21, 1983, abandoned.

TECHNICAL FIELD

This invention relates to methods, apparatus, and substances for the treatment of cancer and particularly to the combined use of hyperthermia and substances in the treatment of cancer.

BACKGROUND OF THE INVENTION

Present modalities of treatment for malignant tumors and particularly malignant brain tumors include amongst others surgery, radiation therapy, and chemotherapy. However, the treatment of malignant brain tumors has a very poor prognosis for survival. Furthermore, the quality of life of survivors during and after treatment is typically poor. Clinical evidence indicates that hyperthermia treatment with modest increases in the temperature of cancerous tissue cells has led to the regression, disappearance, and on some occasions cure of malignant tumors. Hyperthermia is more cytotoxic to neoplastic cells than normal cells, because neoplastic cells are oxygen deprived, nutritionally deficient, and low in pH making them incapable of tolerating the stress imposed by elevated temperature.

The major forms of energy for generating hyperthermia presently include microwaves, radio frequency induction, radio frequency localized current, and ultrasound. Most of the techniques used to dispense these are non-invasive, i.e., the heat generating source is external to the body and does not invade the body. Several problems exist with these non-invasive techniques. First, the energy must pass through the skin surface, and, as a result, a substantial amount of power is absorbed by normal peripheral body tissue. Second, these external heating sources cause nonuniform temperature profiles throughout the tumor and increased temperatures in normal tissue. Nonuniform heating does not assure destruction of the tumor at cold spots. Whereas, unwanted destruction of normal tissue may occur at hot spots.

Studies indicate that tumor mass reduction by hyperthermia is related to the thermal dose. Thermal dose is the minimum effective temperature applied throughout the tumor mass for a defined period of time. Hot spots and cold spots which occur with microwave hyperthermia may cause increased cell death at the hot spots, but ineffective treatment at cold spots results in future tumor growth.

Others have attempted the use of interstitial techniques to obtain local hyperthermia, with limited success. Interstitial heating of brain tumors through an implantable microwave antenna has been investigated. However, microwave probes are ineffective in producing precisely controlled heating of tumors. Temperature may deviate as much as 10 degrees Celsius from the desired target temperature. Besides, microwave activity adversely affects cellular structures and their integration, regardless of other thermal effects. The result is, again, nonuniform temperatures throughout the tumor. Such variations are a result of the microwave antenna's inability to evenly deposit energy throughout the tissue.

Efferent blood flow is a major cause of heat loss for tumors being heated, and blood flow varies throughout the tumor. As a result, uneven heating results even if energy is delivered uniformly throughout the volume of the tumor. To be effective, the application and deposition of thermal energy to the tumor must be precisely controlled to compensate for the variations in blood flow. In addition, the therapy itself will perturb the tumor's vascular system during treatment causing variations in local perfusion around the probe. Thus, heat loss from a tumor will be time dependent and affected by the hyperthermia treatment. This demonstrates the need to both monitor and control the temperature of the tumor throughout treatment.

Another brain tumor treatment, chemotherapy, also has a number of problems. The perfusion of agents from the blood to brain cells is much lower than that from the blood to other cells. This phenomenon, commonly known as the blood-brain barrier, prevents chemotherapeutic agents from effectively treating brain tissue having neoplastic cells. Increasing the concentration levels of these agents in blood, however, does not necessarily result in increased delivery of these agents to the tumor site. Another problem is the damage to normal tissue. This problem is, of course, weighed against the effects of unchecked tumor growth. In addition, the side effects of these high concentration level agents in the patient typically create a poor quality of life during and after treatment. Still another problem is the effective life of the agent, which may be as short as 15 to 20 minutes. Getting a short life agent intravenously to a brain tumor in a timely manner and for an extended period of time complicates the delivery process. Controllably releasing an agent in a cyclical manner further complicates the process.

Studies have shown that elevating the temperature of various chemotherapeutic drugs only a few degrees Celsius increases the effectiveness level of the drug significantly. The added benefits of treating a malignant tumor with these drugs at temperatures elevated above normal body temperatures are significant. However, a major problem is delivering these drugs while either maintaining the temperature thereof at a controlled elevated level for any extended period of time or raising the temperature of the drug to the control level once delivered to the tumor site.

SUMMARY OF THE INVENTION

The foregoing problems are solved and a technical advance is achieved in an illustrative hyperthermia system for treating tissue having neoplastic cells, such as a malignant brain tumor, by the heat activated release of a carried substance interstitially to the tissue, the release occurring at a predetermined temperature above the initial temperature of the tissue. Illustratively, the apparatus of the invention comprises delivery means such as an elongated member of, for example, a probe or catheter that is interstitially implanted in the tissue. Advantageously, the elongated member includes an outer or coating layer of a carrier substance that releases the carried substance interstitially to the tissue when the carrier substance is heated to the predetermined temperature. The heating of the carrier substance to the predetermined temperature allows for the controlled and/or timed release of the carried substance interstitially to the tissue. The elongated member also includes heating means such as an electrical heater element for heating the carrier substance to the predetermined temperature. To advantageously control the release and timing of the carried substances, the elongated member further includes sensor means such as an electrical thermistor for measuring the temperature of the member, which is affected by the temperature of the surrounding tissue. The probe also includes a plurality of conductors within the elongated member for delivering power to the electrical heater element and thermistor. Connected to the conductors are a plurality of electrical terminals that are connectable to a power supply and electrical metering equipment. Advantageously, the measurement of the power delivered to the heater element and of the probe temperature are utilized to determine the perfusion of the treated tissue.

Any one of several different techniques is utilized for including the carried substance with the probe. In one embodiment, the carried substance, such as an anti-cancer drug, is mixed with a solution of the carrier substance. The probe is dipped in the mixed solution and removed to form a coating layer thereon. The coating layer adheres to the surface of the probe by simply drying thereon in situ. Alternatively, the carried substance is initially applied to the surface of the probe, which is then covered or coated with the carrier substance.

Another technique for including the carried substance with the probe is by attaching or chemically bonding the carried substance to the carrier substance. The carrier substance, in turn, is then attached to the probe. The application of heat causes the carrier substance at the predetermined temperature to release the drug interstitially to the tissue.

Another technique for including the carried substance with the probe is by encapsulating. The carried substance is encapsulated by the carrier substance, which adheres or attaches to the surface of the probe. The type and size of the carrier substance is advantageously selected to control the temperature at which the carried substance is released. Several different types and sizes of heat activated encapsulating substances are joined with the surface of a probe for a cyclical or timed release of the carried substance.

Still another technique for including the carried substance with the probe involves the use of a micropore membrane. In one embodiment, the carrier substance membrance covers the elongated member portion of the probe, which includes a port therein for injecting the carried substance between the surface of the probe and membrane. In another embodiment, the membrane covers carrier substance capsules joined with the surface of the probe. When heated, the carrier substance capsules release the carried substance which then diffuses through the membrane.

From another aspect, the apparatus comprises a probe having an elongated member that is interstitially implanted in a malignant tumor. Advantageously, the elongated member is coated with a carrier substance that is responsive to tissue fluid for releasing an anti-cancer drug for providing one form of treatment. Furthermore, the probe also includes means such as an electrical heater element for applying heat to the tissue for providing a second treatment of the tissue. As a result, the effectiveness level of the two treatments in combination is greater than the effectiveness level of either one of the drug and heat treatments individually.

In one illustrative embodiment, the carrier substance of the probe is chosen to release the drug when in contact with tissue fluids. Alternatively, the carrier substance is chosen for controlled release of the drug over a predetermined period of time when in contact with the tissue to maintain a desired effectiveness level of the drug over the time period. Heating the tumor also elevates the temperature of the anti-cancer drug to advantageously increase the effectiveness level of the drug treatment. Drug dispersion is also increased at the elevated temperatures.

To advantageously maintain the temperature of a predetermined volume of tissue surrounding the probe at a minimum predetermined level, the probe includes sensor means such as a thermistor for measuring the temperature of the probe and conductor means for measuring the power delivered to the probe. The problems of perfusion are thus minimized thereby maintaining the predetermined tissue volume at a minimum temperature. Consequently, a minimal thermal dose, as well as drug concentration, is maintained, thereby reducing undesirable side effects that may be experienced by a patient.

The elongated member of the probe also advantageously comprises a thermally conductive material for distributing the heat across the surface of the probe to reduce hot spots within the treated tissue.

This invention also includes a method of treating the tissue with a substance that is released from an interstitially implanted probe at a predetermined temperature above the temperature of the tissue. Advantageously avoiding the blood-brain problem and increasing the effectiveness level of a therapeutic carried substance at normal tissue temperatures, the method comprises interstitially implanting the elongated member of a probe in the tissue and heating the member to a predetermined temperature above the normal temperature of the tissue. At the predetermined temperature, the member releases the substance for providing a treatment of the tissue. Furthermore, heating the probe member also provides for heating the surrounding tissue to a minimum temperature for providing a second treatment of the tissue. To advantageously maintain the temperature of the tissue at the minimum temperature, the temperature of the probe is measured to regulate the power required to heat the probe and surrounding tissue and to control the effects of blood perfusion.

From another aspect, the method comprises interstitially implanting an elongated member of the probe in the tissue and advantageously releasing the drug from the member directly to the tissue when the member is in contact with tissue fluids. As a result, this solves the blood-brain barrier problem associated with intravenous delivery of a chemotherapeutic agent. The heater element of the probe is then energized to heat the tissue and to provide a second treatment of the cancerous cells.

A further advantage of the heat treatment is elevating the temperature of the drug to increase the effectiveness level of the drug treatment.

A carrier coating is selected to release the drug over a desired time period in response to the heat. The temperature of the heat applied thus advantageously regulates the rate at which the drug is released.

The method also includes measuring the power delivered to the probe and the temperature of the probe to advantageously maintain the tissue at a minimum effective treatment temperature. Thus, the effects of perfusion and cold spots within a malignant tumor are eliminated. Furthermore, the measuring process is also used to control the effectiveness level of the drug treatment.

The invention also includes a substance for treating the tissue. The substance includes a drug for treating the tissue and a carrier substance responsive at a predetermined temperature above tissue temperature for releasing the drug interstitially to the tissue. The carrier substance includes molecules for either mechanically adhering to the surface of a probe or chemically bonding to the molecules of the probe. With one group of carrier substances selected from the group consisting of carbohydrate-, protein-, nucleotide-, and fatty acid based molecules, the carrier substance mixes with the drug to hold the drug in position without chemically altering or bonding to the drug. With the application of heat, the carrier substance will either melt, peel off, disintegrate, or break down allowing exposure of the drug interstitially to the tissue.

With another group of carrier substances selected from the group consisting of polypeptide-, protein-, carbohydrate chain, and fatty chain-based molecules, one end of the carrier substance molecule attaches or bonds to a molecule of the elongated member portion of the probe, and the other end or ends of the carrier molecule attaches to a drug molecule. Here, under the stimulus of heat, the carrier molecule releases the drug molecule by a simple unfolding of the attaching end of the molecule by hydrolysis or bond cleavage of the carrier molecule. The substances from this group may also be combined to form mixtures such as glycoproteins.

Another carrier substance is a fatty acid chain for microencapsulating the drug and attaching the microcapsule to the surface of the probe. By changing the number of carbon atoms in the chain, the temperature at which the fatty acid (lipid) membrane melts or dissolves is advantageously controlled.

Another form of the carrier substance is a micropore membrane for surrounding the probe to which the drug has already been applied. The combination of moisture in the tissue and the application of heat gradually releases the drug from the probe surface, thereby allowing a slow diffusion of the drug through the micropore membrane into the tissue. Alternatively, the membrane covers the entire length of the elongated member portion with a port on the surface thereof through which the drug is injected between the surface of the probe and the membrane.

DETAILED DESCRIPTION

Figures 1, 2:
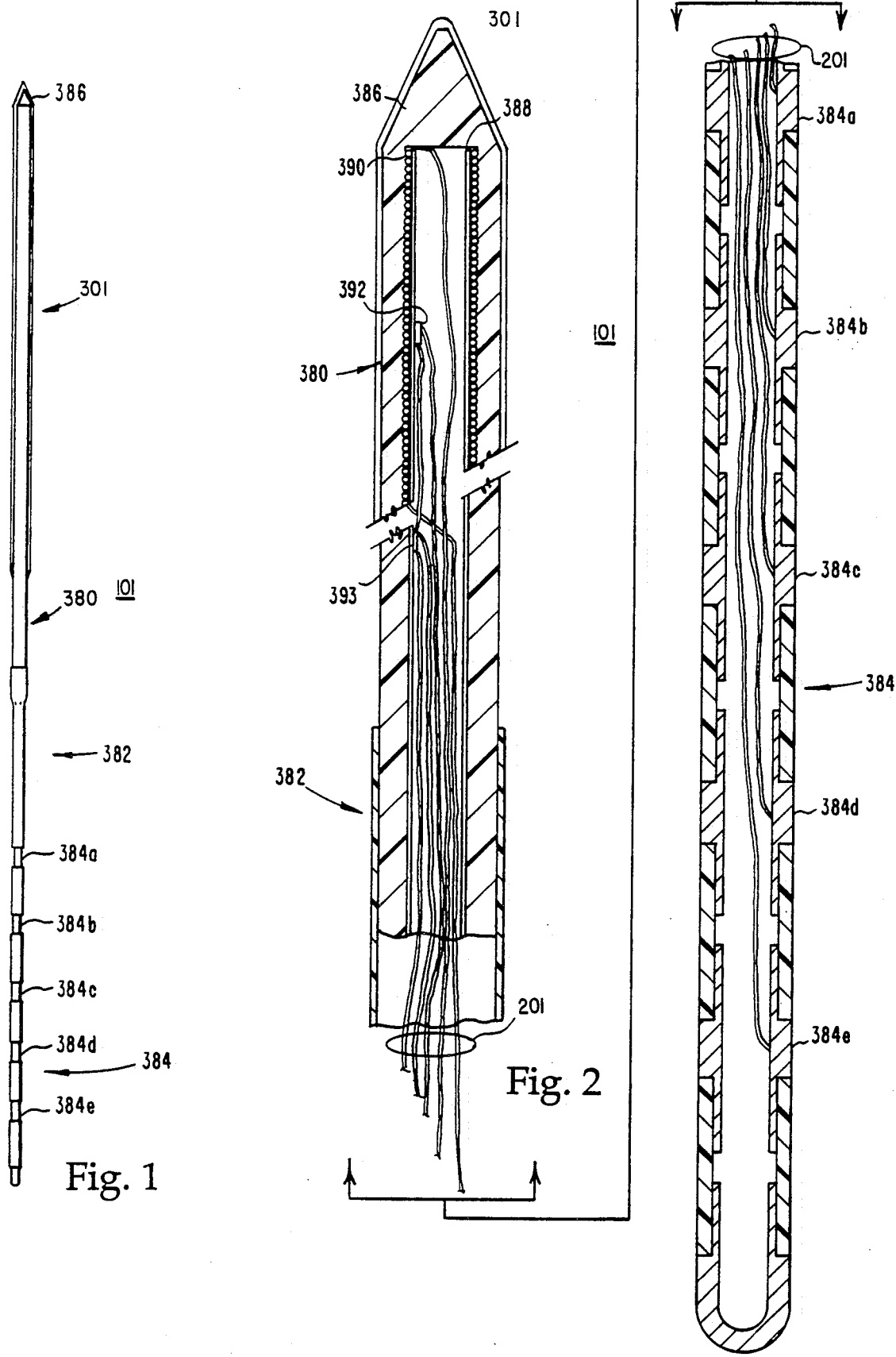
FIGS. 1 and 2 are side views of an illustrative probe.

Depicted in FIGS. 1 and 2 is a probe 101, also referred to as a catheter, for interstitially implanting into tissue having malignant neoplastic (cancer) cells such as a malignant brain tumor. The implantable probe consists of a semi-rigid portion 380 which is directly implanted into the tumor, a flexible portion 382 which remains outside the body, and a connector portion 384 for mating to a manifold connector (not shown). The manifold connector in turn connects to a control system (not shown) which energizes a wire-wound heater element 390 that is positioned within the elongated member portion 380. An illustrative hyperthermia system including the manifold connector and control system are described in U.S. patent application, Ser. No. 193,167, filed May 2, 1988, of the present inventors, which is herein incorporated by reference. In addition, the control system monitors the temperature of the probe, as well as the surrounding tissue, and the power delivered thereto for maintaining a minimum temperature throughout the tissue which the probe is implanted therein. The semi-rigid portion of the probe is coated with an outer or coating substance layer 301, including a carrier and a carried substance. The carrier substance transports molecules of the carried substance such as a therapeutic drug within its molecular structure and also adheres to the outer surface of the semi-rigid portion. When the probe is implanted in the tissue, the carrier substance releases at a predetermined temperature, typically above 37° C., the therapeutic drug to the tissue having the neoplastic cells. The release of the carried substance or the rate at which it is released is controlled by any one or more of several factors including contact with the fluids of the tissue and the application of heat to the carrier substance from the heater element of the probe. Furthermore, the application of heat to the malignant tumor is also used to provide a second form of treatment.

Semi-rigid elongated member portion 380 has been designed to give the proper rigidity for insertion balanced with the desired flexibility for implantation. The flexible portion 382 prevents injury to the tissue adjacent to the probe by minimizing torque transmission from the manifold connection. The probe has been designed with the smallest possible diameter to minimize disturbance of tissue, displacement or destruction of important structures, and injury to blood vessels and yet large enough to adequately conduct heat with acceptable surface temperatures. The tip 386 of the probe has been tapered so that the tip selects a point of penetration into the tissue and the rest of the probe follows the same path, minimizing distortion of tissue and injury to the blood vessels.

Coating layer 301 substantially covers semi-rigid portion 380 and includes a carrier substance for releasing a carried substance to the tissue in which the probe is implanted therein. The carried substance is any drug, chemotherapeutic agent, synthesizer, inhibitor of chemical activities, enzyme, catalytic agent, or any other substance that when released in the interstitium into which the probe is implanted, will effect the tissue in a desired or beneficial manner. Furthermore, the carried substance may also comprise an anesthetic for relieving pain.

By way of one example, the carrier substance is any type of carrier molecule or compound that adheres to or joins with the surface of the probe without chemically interacting or bonding with the molecules of the probe or the carried substance. In one case, the carried substance is first applied to the surface of the probe, and then the carrier substance is applied to cover or coat the carried substance layer. In another case, a solution of the carried and carrier substances are mixed and applied to the outer surface of the probe. After application, the mixture dries in situ. In such example, the carrier substance is selected from a group consisting of well-known and commercially available carbohydrates, fatty acids, proteins, nucleotide, or any other organic substance that can adhere to the surface of the probe as well as transport the molecules of the carried substance without chemically interacting or bonding therewith. When heat is applied, the carrier substance will either melt, peel off, disintegrate, or break down (i.e., by hydrolysis or bond cleavage), thereby releasing the carried substance interstitially to the tissue. One characteristic of the carrier substance is that the molecular structure of this adherent gradually allows release of the molecules of the carried substance for which it is acting as a carrier. By regulating the temperature of the probe, the duration of the heat application, or a combination of both, a graded release of the carried molecules is obtained.

By way of a second example, the carrier substance comprises a compound or molecules that attach or chemically bond to the carried substance and the surface of the probe. Illustratively, one end of the carrier molecule attaches or bonds to the surface of the probe, and the other end (or multiple ends) attaches or bonds to a carried substance molecule. With the application of heat, the carrier molecule releases the carried molecule by a simple unfolding of the attaching end of the molecule by hydrolysis or bond cleavage of the carried molecule. In such second example, the carrier substance is selected from a group consisting of well-known and commercially available polypeptides, proteins, carbohydrate chains, fatty chains, or a mixture thereof such as glycoproteins.

By way of a third example, the carrier substance comprises a microcapsule. The outside surface of the microcapsule adheres or attaches to the surface of the probe, whereas the inner surface of the microcapsule adheres or attaches to the carried substance molecules. When heat is applied, the microcapsule either opens, dissolves, or melts thereby releasing the carried substance interstitially to the tissue. The microcapsule carrier substance is selected from a group consisting of polypeptides, proteins, carbohydrates, glycoproteins, or fatty acid substances. Presently, microencapsulation technology has been better developed for fatty acid chains. The advantage of fatty acid chains is that by changing the number of carbon atoms in the chain, the temperature at which a fatty acid (lipid) membrane melts or dissolves is readily controlled. Microcapsules of the same substance can be made of different sizes with different melting temperatures so that the timed release of the carried substance is controlled by varying the temperature of the applied heat. This is particularly advantageous when treatments are cyclical and occur over an extended period of time. Different carrier substances are used to form different types or sizes of microcapsules which permit not only the transport of different types and sizes of carried substances, but also control the release of the carried substances in time and space by varying the temperature of the applied heat.

A fourth example of the carrier substance is a well-known micropore membrane covering a probe with a layer of the carried substance already adhered thereto. The application of heat releases the carried substance from the surface of the probe. When released, the carried substance diffuses through the micropore membrane with the tissue fluid. The micropore membrane may also be combined with microcapsules to provide a broad range of release periods and temperatures.

In another example, the micropore membrane substantially covers the entire length of the elongated member. The member includes a port through which carried substances are injected between the membrane and the outer surface of the probe.

Depicted in FIG. 3 is an enlarged view illustrating coating layer 301 and a cross section portion of semi-rigid portion 380. As shown in FIG. 3(a), molecules 302 of the carried substance are simply suspended by molecules 303 of the carrier substance which adheres to the outer surface of semi-rigid portion 380. One example of providing this coating layer is to mix an aqueous solution of the carrier and carried substance such as a carbohydrate and a therapeutic drug, dipping the semi-rigid portion of the probe in the solution, removing the probe with the solution thereon, and allowing the solution to dry thereby forming the desired coating layer.

Figure 3A:
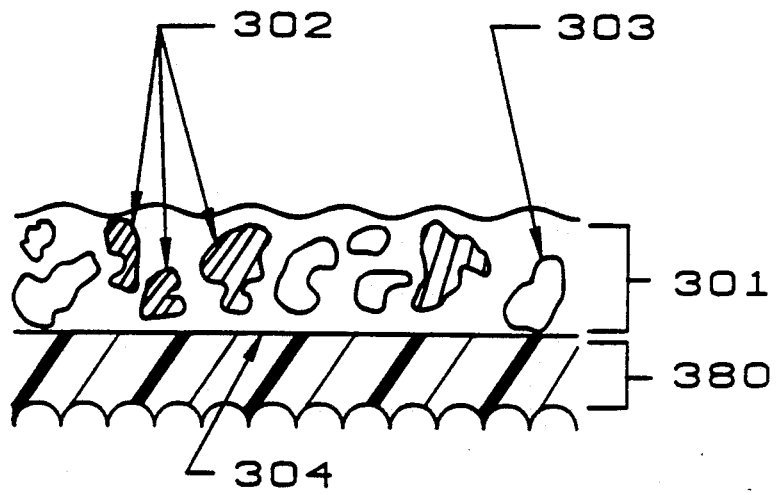
FIGS. 3(a)—3(e) show sectional views of the outer or coating layer on the surface of the probe of FIG. 1.
Figure 3B:
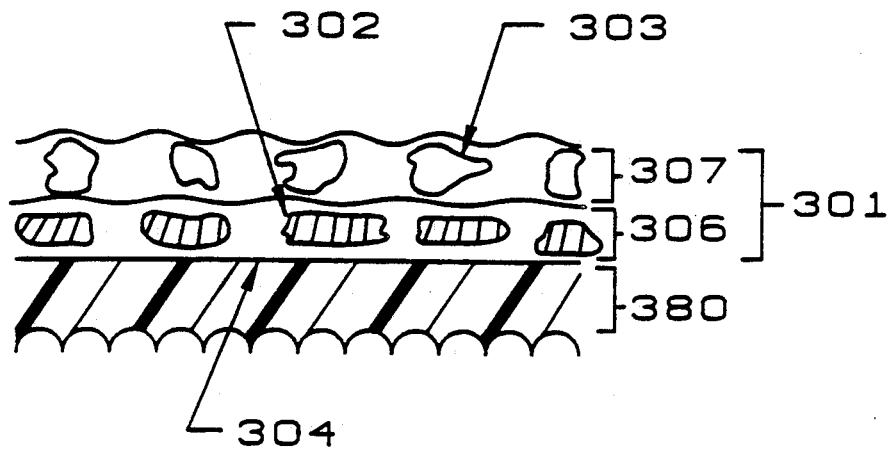

As shown in FIG. 3(b), molecules 302 of the carried substance form a layer 306 which adheres to outer surface 304 of semi-rigid portion 380 of the probe. One method of forming carried substance layer 306 is to dip semi-rigid portion 380 into a solution of the carried substance, removing the solution of the carried substance, and allowing the solution to dry in situ thereby forming layer 306. A similar technique is employed to form layer 307 of carrier substance molecules 303 20 covering carried substance layer 306.

Figure 3C:
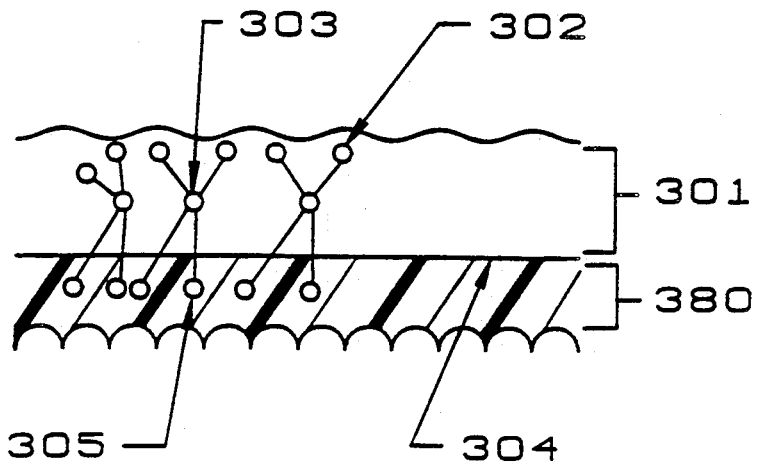

As shown in FIG. 3(c), the carrier molecules 303 are chemically bonded or linked to molecules 305 of semi-rigid portion 380 and molecules 302 of the carried substance. As shown, carrier agent molecules 302 link to molecules 303 of semi-rigid portion 380 thereby attaching coating layer 301 to outer surface 304 of the semi-rigid portion. Furthermore, carrier agent molecules 303 are also linked to carried substance molecules 302 for delivering the carried substance to the affected tissue when the probe is implanted therein. The carrier agent is selected to be biocompatible with the brain and other bodily tissues. Other desired characteristics of the carrier substance is that it should be nonantigenic, biodegradable, non-active biologically, and have a dense adhesion to the surface of the semi-rigid portion. It is also desirable that the carrier substance be mechanically friction (rub) resistant and should withstand a sterilization process.

Figure 3D:
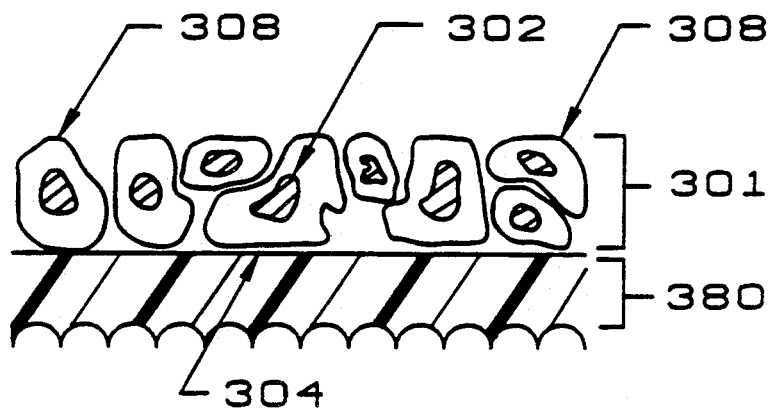

As shown in FIG. 3(d), well-known and commercially available carrier substance microcapsules 308 form layer 301. The outside surface of each microcapsule adheres or attaches to surface 304 of the probe. Carried substance molecules 302 adhere or attach to the inside surface of the microcapsule. When heated to a temperature above normal tissue temperature, the microcapsules open releasing the carried substance to the tissue. Nitrosourea BCNU (carmustine) is one example for use as the carried substance in the microcapsules.

Figure 3E:
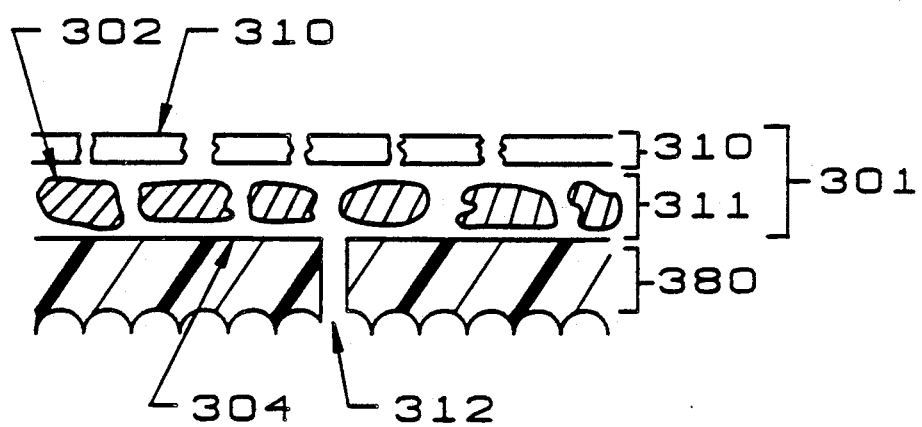

As shown in FIG. 3(e), well-known and commercially available carrier substance micropore membrane 310 forms a layer over a layer 311 of carried substance molecules 302. The carried substance molecules 302 are positioned by one of several different methods. The first method, as previously discussed, involves dipping rigid portion 380 into a solution of the carried substance and allowing the solution to dry and form the layer. Micropore membrane 310 is then applied over the dried carried substance layer. Another method involves injecting the carried substance through port 312 of the semirigid portion with the micropore membrane already positioned on the surface of the probe. The injected carried substance forms a layer between the micropore membrane and surface 304 of the probe.

Returning the reader's attention to FIG. 2, the probe provides the medium to introduce heat energy into the tumor environment. Within the semi-rigid portion 380 of the probe is a cylindrical, thermally conductive plastic (preferably polycarbonate) tube 388 around which a resistive heater element wire 390 is wound and in which an accurate thermistor 392 is positioned. The resistive heating element directly heats the thermistor through the conductive material of tube 388. The heating element and thermistors 392 and 393 are connected to the external control system circuitry by a plurality of insulated electrical conductor wires 201 which extend through the semi-rigid and flexible portions to the end connector portion 384. More specifically, heater 390 has one end connected to connector terminal 384a and another end connected to terminal 384b. Thermistor 392 has one lead connected to terminal 384c and another lead connected to terminal 384d. Thermistor 393 has one lead connected to terminal 384d and another lead connected to terminal 384e.

Approximate typical probe dimensions which have been found useful in brain tissue are as follows: 9-12 cm for the semirigid portion, 5 cm for the flexible portion, 1-10 cm for the heater coil, and 2.2 mm for probe outer diameter.

The semi-rigid outersheath portion 380 of the probe is constructed of high-density polyethylene material or other suitably conductive material because of the need for heat transfer and temperature response. The semi-rigid portion also buffers the heat passing through allowing a more uniform heat distribution across the outer surface to reduce the effects of wire-wound heaters. The thermal buffer effect of the outer sheath further protects blood vessels and tissue from high temperatures. As the heat transfer away from the outer sheath increases, the temperature of the outer surface decreases with respect to the heater temperature. In such case as where a major blood vessel is adjacent to the probes, excessive heat will not be conducted to the flowing blood, because the heat transfer will be limited by the outer sheath. However, within normally perfused or typical tumor tissue the surface temperature is elevated and can be carefully controlled. The surface temperature can be calculated from the power delivered and the physical properties of the probe. More specifically, the perfusion is calculated from the measured power delivered to the heater element and the measured temperature from the thermistor.

The coated probes are stereotaxically placed in the tumor in a predetermined pattern for volumetric heating, with an imaging system being used for guidance in the placement of probes. In this regard, it should be noted that the preferred embodiment of the present invention is described here in terms of a method and apparatus for producing both a hyperthermia and a thermally elevated drug treatment within the brain, but that the invention may be also applicable to the neck, the chest cavity, the long bones of the body, or to other points of interest, including those not easily accessible because of overlying bones or delicate organs. Image-based stereotaxic placement of the probes is performed with an imaging system of the type having a gantry with a horizontal, cylindrical throat axially aligned with a movable patient cradle. A computerized tomography (CT) scanner is a well known form of such an imaging system and will therefore be used as a reference herein for the description of the preferred embodiment, although other imaging systems and techniques may be used, such as X-ray film, X-ray fluoroscopy, magnetic resonance imaging, electromagnetic imaging and ultrasound.

Figure 5:
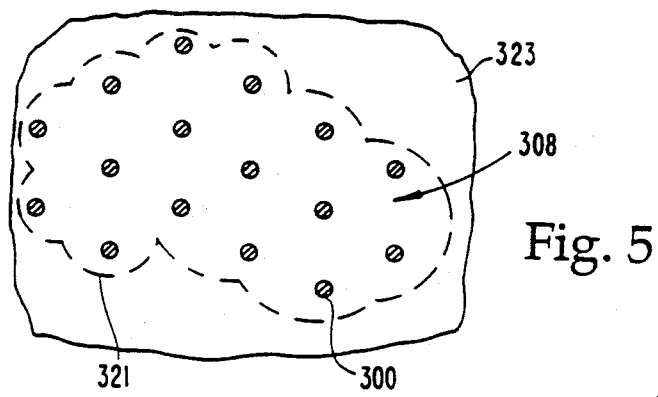
FIG. 5 is a sectional view taken along the lines 10—10 of FIG. 4.
Figure 4:
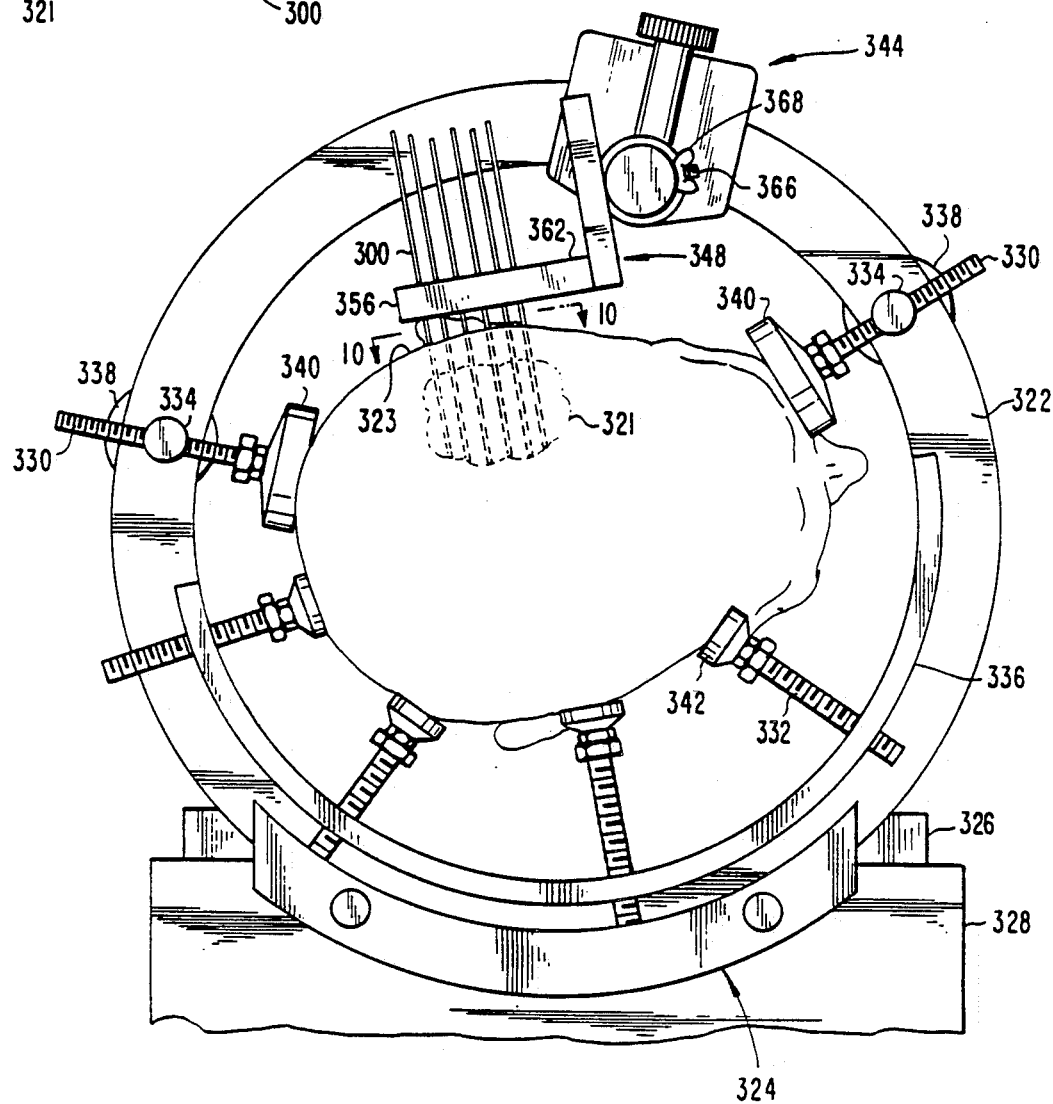
FIG. 4 shows a head end view of a patient lying on a patient cradle with a support frame in place for use in stereotaxic placement of probes according to the preferred embodiment of the present invention.

FIG. 4 shows a head end view of a patient lying on a patient cradle with a support frame in place for use in stereotaxic placement of probes according to the present invention. In the illustrated view, six probes 300 are visible extending into a brain tumor 321. Ten other probes are hidden from view in the background of FIG. 4, for a total of 16 probes in this example, as shown in FIG. 5, which is a sectional view taken along lines 10—10 of FIG. 4, i.e., an axial view of the array of probes 300. Only the skull portion 323 immediately surrounding the tumor mass 321 is shown in the drawing. FIG. 5 illustrates the preferred probe pattern for volumetric heating of the illustrated tumor 321. As used herein, volumetric heating means heating an entire volume of a target mass above a minimum temperature.

Figure 6:
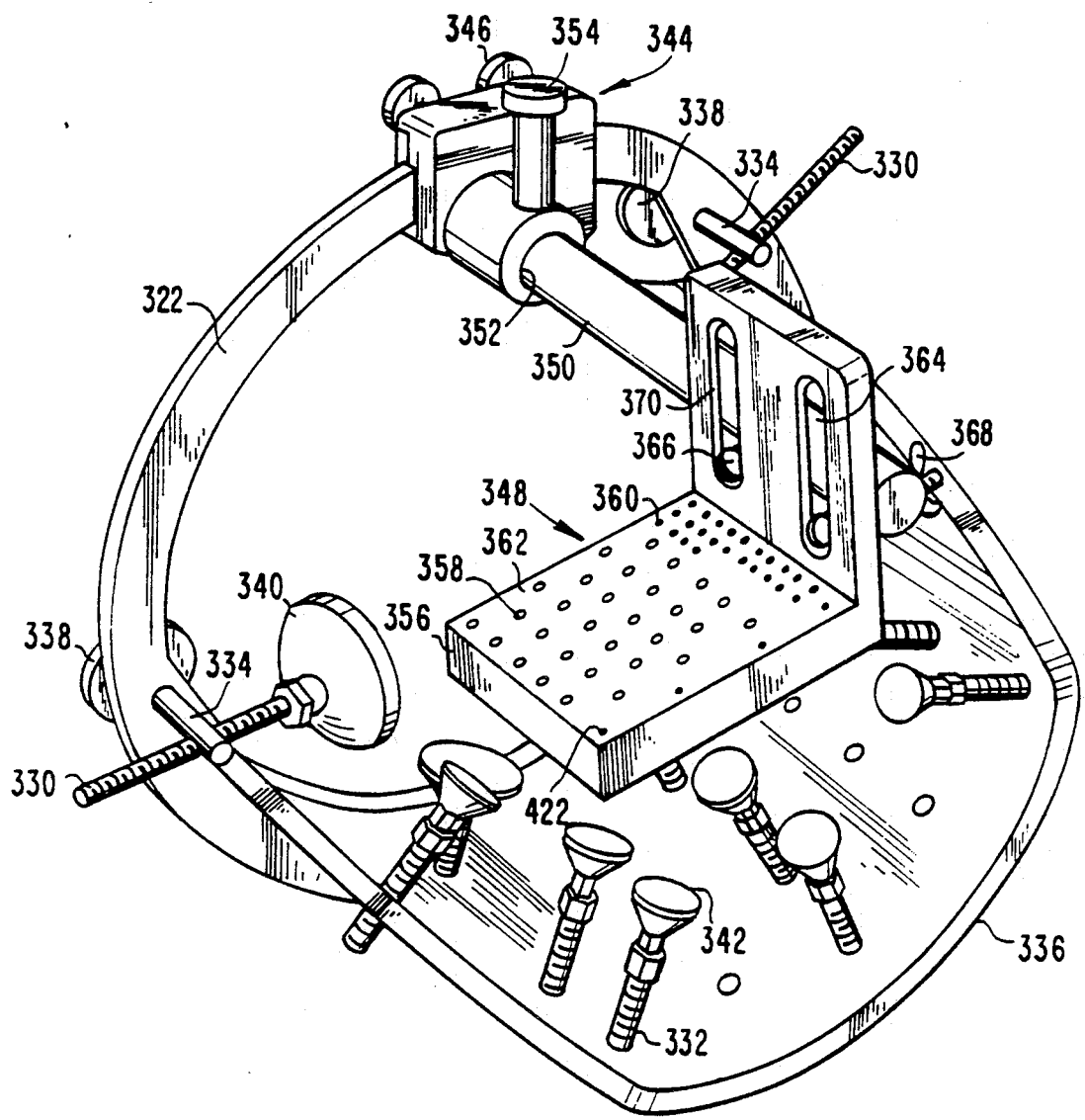
FIG. 6 is a perspective view of the support frame shown in FIG. 4.

The support frame for the patient's head includes a ringlike member or ring 322 encircling the head and clamped on its lower end to a ring mount generally designated 324. An adapter 326 mounts ring mount 324 to the head end 328 of the patient cradle. The details of the structure for mounting the ring frame to the patient cradle are disclosed in U.S. Pat. No. 4,360,028, which patent is hereby incorporated by reference. With combined reference to FIG. 4 and to FIG. 6, which shows a perspective view of the support frame, the support frame includes upper support rods 330 and lower support rods 332 mounted to ring 322 by spacers 334 and plastic shell 336, respectively. Upper support rods 330 are threadably engaged in spacers 334 which are mechanically linked to knobs 338. Each upper support rod 330 has a plastic cushion 340 pivotally mounted on one end. Patient support rods 332 each have a threaded shaft threadably engaged in shell 336 and a cone-shaped cushion 342 mounted on one end as shown. The support frame also includes a template carriage 344 slidably mounted on ring 322. Two tension knobs 346 are provided for clamping carriage 344 in a desired position on ring 322. A template 348 is mounted on a tubular extension arm 350 rotatably and slidably mounted in a bore 352 extending through template carriage 344 in a direction perpendicular to the plane of ring 322. Tension knob 354 is provided to look extension arm 350 in a desired position within bore 352. Template 348 includes a main template block 356 formed of a radiolucent material and provided with an array of holes 358 for probe guidance and a set of holes 360 for optically coded identification of the orientation of the template in any particular image produced by the imaging system. Holes 358 and 360 all extend through template block 356 in a direction perpendicular to the top surface 362 thereof. Template 348 further includes a pair of slots 364 for vertical movement of template 348 with respect to tubular extension arm 350, the template being secured to extension arm 350 with a pair of bolts 366 and a pair of wing nuts 368 attached respectively thereto, each of the slots being provided with a seat 370 to restrain the head of bolt 366. In operation, after a patient has been placed on the patient cradle in a desired position with the head oriented, supported and restrained in a desired manner in the support frame, template 348 is moved into a desired position and orientation with respect to a tumor by adjustment of template carriage 344 on ring 322 and of tubular extension arm 350 within bore 352 of template carriage 344 and adjustment of the position of bolts 366 in slots 364 of the template. When the template is positioned, it is used as a guide for drilling entry holes through the patient's skull in line with predetermined locations in the tumor to be treated, and then a probe is interstitially implanted by insertion through each of the drilled holes.

When the probe has been interstitially implanted within the brain tumor, the carrier substance coating on the probe releases the drug from the carrier to the tissue when the carrier reaches a predetermined temperature above normal tissue temperature. The drug when released provides a treatment of the neoplastic cells included in the tumor tissue. The control system of the hyperthermia system energizes the heater element of the probe for heating the probe and carrier substance. The heat from the heater element then provides a second treatment of the neoplastic cells. Dependent on the selection of the carrier substance coating, the drug may also be released in response to the interstitial fluid of the tumor and the heat from the heater element. Both methods may be used in combination to release the drug from the carrier substance over a given period of time. To elevate the temperature of the drug and thereby increase its effectiveness level, the heater element of the probe is energized to heat not only the tissue but the therapeutic drug as well. Furthermore, the carrier substance also responds by releasing the therapeutic drug over a shorter period of time. In addition, heating the tissue increases the susceptibility of the tissue to the carried substance. Elevating the tissue temperature also increases the cellular metabolic rate and, therefore, increases the effectiveness and the effects of the carried substance.

By monitoring the temperature of the probe and surrounding environment along with the power delivered to the probe, a minimum temperature is maintained throughout the surrounding volume including the tissue. By regulating the temperature of the probes, the duration of heat application, or a combination of both, a graded release of the carried molecules is obtained along with maintaining the temperature of the treated tissue at a minimum level.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. The carried and carrier substances have been described as forming one or more layers on the surface of the probe. However, the invention is not so limited. The carrier and carried substances may be integrated into semi-rigid portion 380 of the probe.

What is claimed is:

1. A probe for treating a cancerous tumor comprising:
   an elongated member sized for and having a distal end tapered for interstitially implanting said elongated member in said cancerous tumor;
   a heater element positioned about said distal end for producing heat; and
   a coating layer joined with said member about said distal end and responsive to said heat for releasing at a predetermined temperature above a temperature of said tumor a drug for providing a treatment of said tumor.

2. The probe of claim 1 wherein said coating layer includes said drug.

3. The probe of claim 1 wherein said coating layer comprises a substance responsive at said predetermined temperature for releasing said drug.

4. A probe for treating tissue having neoplastic ells comprising:
   an elongated member having a distal end tapered for interstitially implanting said member in said tissue;
   a carrier joined with an outer layer of said member about said distal end and responsive to said tissue for releasing a drug for treating said neoplastic cells; and
   a heater element positioned about said distal end for thermally conducting heat to further treat said neoplastic cells.

5. The probe of claim 4 further comprising said drug.

6. The probe of claim 4 further comprising a sensor having an electrical characteristic that changes in response to changes in temperature for measuring a temperature of said probe.

7. The probe of claim 4 wherein said elongated member comprises a semi-rigid thermally conductive material for distributing said heat across said outer layer in a predetermined manner.

8. The probe of claim 4 wherein said carrier comprises a substance for adhering to said outer layer and responsive to said tissue for releasing said drug over a predetermined period of time to said tissue.

9. A method of treating tissue having neoplastic cells with a probe having an elongated member including an outer layer for releasing a drug and a heater element for heating said elongated member, comprising the steps of:
   interstitially implanting said elongated member in said tissue;
   releasing said drug from said outer layer to said tissue when said member is interstitially implanted in said tissue, said drug for providing a treatment of said neoplastic cells;
   energizing said heater element for producing said heat; and
   heating said tissue to a first predetermined temperature in response to said heat for providing a second treatment of said neoplastic cells.

10. The method of claim 9 wherein said drug treatment of said neoplastic cells has a first predetermined effectiveness level and said method further comprises heating said drug to a second predetermined temperature in response to said heat for increasing the effectiveness level of said drug treatment to a second predetermined level greater than said first level.

11. The method of claim 9 wherein said probe further includes a sensor for measuring the temperature of said member and wherein said method further comprises measuring the temperature of said member.

12. A method of treating tissue with a probe having an elongated member including an outer layer responsive at a predetermined temperature above a tissue temperature for releasing a substance and also having a heater element for heating said elongated member; comprising the steps of:
   interstitially implanting said elongated member in said tissue;

heating said outer layer of said elongated member to said predetermined temperature above a temperature of said tissue; and releasing from said outer layer at said predetermined temperature said substance interstitially to said tissue, said substance for providing a treatment of said tissue.

13. The method of claim 12 further comprising heating said tissue to a second predetermined temperature with said elongated member for providing a second treatment of said tissue.

14. The method of claim 13 further comprising measuring the temperature of said elongated member for maintaining said tissue at said second predetermined temperature.

15. Apparatus for treating tissue comprising:
an elongated member having a coating, said coating comprising a carrier substance responsive at a predetermined temperature above a temperature of said tissue for releasing a carried substance interstitially to a tissue, said elongated member sized for and having an end tapered for interstitially implanting said elongated member in said tissue; and
said elongated member including therein a heater element for heating said carrier substance to said predetermined temperature above said tissue temperature.

16. The apparatus of claim 15 wherein said elongated member further includes a sensor for measuring the temperature of said elongated member.

17. The apparatus of claim 16 further comprising said carried substance.

18. Apparatus for treating tissue having cancerous cells comprising:
an elongated member having a distal end for interstitially implanting said member in said tissue;
carrier means joined with said member about said distal end and responsive at a first predetermined temperature above a second tissue temperature for releasing a drug interstitially to said tissue, said drug for providing a treatment of said cancerous cells; and
means for heating said carrier means to said first predetermined temperature.

19. The apparatus of claim 18 wherein said means for heating comprises an electrical heater element positioned within said elongated member.

20. The apparatus of claim 18 wherein said elongated member comprises a semi-rigid conductive material for heating said carrier means in a predetermined manner.

21. The apparatus of claim 18 further comprising sensor means positioned within said elongated member for measuring temperature.

22. The apparatus of claim 21 further comprising means for measuring power delivered to said means for heating.

23. The apparatus of claim 22 further comprising said drug.

24. The apparatus of claim 18 wherein said carrier means comprises a carrier substance responsive at said first temperature above said tissue temperature for releasing said drug interstitially to said tissue.

25. The apparatus of claim 24 wherein said carrier substance includes at least one type of molecule selected from the group consisting of polypeptide-, protein-, and carbohydrate chain-based molecules.

26. The apparatus of claim 24 wherein said carrier substance includes at least one type of molecule selected from the group consisting of carbohydrate-, protein-, nucleotide-, and fatty acid-based molecules.

27. The apparatus of claim 24 wherein said carrier substance includes molecules for attaching to molecules of said elongated member and also for attaching to molecules of said drug.

28. The apparatus of claim 24 wherein said carrier substance includes molecules for encapsulating molecules of said drug.

29. The apparatus of claim 28 wherein said molecules of said carrier substance for encapsulating said molecules of said drug includes a surface for adhering to a surface of said elongated member.

30. The apparatus of claim 24 wherein said drug includes molecules for adhering to a surface of said member and wherein said carrier substance comprises a micropore membrane surrounding said drug for diffusing said drug into said tissue.

31. The apparatus of claim 24 wherein said elongated member includes a surface having a port therein; wherein said carrier substance comprises a micropore membrane for surrounding said surface of said elongated member having said port therein; and wherein said drug is injected through said port between said micropore membrane and said member surface.

32. The apparatus of claim 24 wherein said carrier substance includes a chain of fatty acid molecules.

33. An elongated member for use with tissue treatment apparatus and serving to provide a first modality, said first modality for providing a first treatment of tissue, and said member also serving to provide at least one additional modality for providing further treatment of said tissue, characterized in that said member is sized and has a distal end for insertion interstitially in said tissue and that said modalities are provided concomitantly and are arranged so that said additional modality is activated by said first modality.

34. A member according to claim 33, characterized in that said first modality includes a heating arrangement for thermal conductive heating of said tissue.

35. A member according to claim 34, characterized in that said additional modality includes carried and carrier substances joined with an outer layer of said member, said carrier substance being responsive to the thermally conductive heating for releasing into said tissue said carried substance for said further treatment.

36. An elongated member according to claim 34 characterized in that said heating arrangement within said member is connected to a separate power supply to provide hyperthermia treatment, and in that the said further treatment involves the release of chemical treatment material, the release being activated by said heating arrangement when said member is inserted in said tissue.

37. An elongated member for use with tissue treatment apparatus and serving to provide a first modality, said first modality for providing a first treatment of tissue, and said member also serving to provide at least one additional modality for providing further treatment of said tissue, characterized in that said member is sized and has a distal end for interstitially inserting said member in said tissue and that said modalities are arranged so that said first and further treatments are provided concomitantly for improving the combined effectiveness of said first and further treatments.

38. A member according to claim 37, characterized in that a passageway longitudinally extends in said member, and in that said passageway serves to selectively receive heating means.

39. A member according to claim 38, characterized in that apertures are provided between the said passageway and the outer surface of said member in order to permit chemical material to be implanted in said tissue.

* * * * *